United States Patent [19]

Sangokoya et al.

[11] Patent Number: 5,157,008
[45] Date of Patent: Oct. 20, 1992

[54] HYDROCARBON SOLUTIONS OF ALKYLALUMINOXANE COMPOUNDS

[75] Inventors: Samuel A. Sangokoya; Milham S. Howie; Aaron L. Dunaway, all of Baton Rouge, La.

[73] Assignee: Ethyl Corporation, Richmond, Va.

[21] Appl. No.: 739,225

[22] Filed: Aug. 1, 1991

[51] Int. Cl.$^5$ ............................................. C08F 4/64
[52] U.S. Cl. ..................................... 502/111; 502/117; 502/152; 556/179
[58] Field of Search ................. 502/111, 117, 152; 556/179

[56] References Cited

U.S. PATENT DOCUMENTS

| | | | |
|---|---|---|---|
| 3,242,099 | 3/1966 | Manyik et al. | 252/429 |
| 3,639,378 | 2/1972 | Long | 260/93.7 |
| 4,189,402 | 2/1980 | Rekers et al. | 252/428 |
| 4,377,720 | 3/1983 | Langer | 585/327 |
| 4,490,514 | 12/1984 | Hoff et al. | 526/165 |
| 4,772,736 | 9/1988 | Edwards et al. | 556/179 |
| 4,937,217 | 6/1990 | Chang | 502/111 |
| 4,952,540 | 8/1990 | Kioka et al. | 502/9 |
| 4,960,878 | 10/1990 | Crapo et al. | 556/179 |
| 5,041,583 | 8/1991 | Sangokaya | 556/179 |
| 5,041,584 | 8/1991 | Crapo et al. | 556/179 |
| 5,043,515 | 8/1991 | Slaugh et al. | 585/512 |

FOREIGN PATENT DOCUMENTS

| | | |
|---|---|---|
| 279586 | 11/1988 | European Pat. Off. . |
| 393358 | 10/1990 | European Pat. Off. . |
| 260602 | 12/1985 | Japan . |
| 1258686 | 4/1989 | Japan . |
| 3103407 | 4/1991 | Japan . |
| 8802378 | 4/1988 | World Int. Prop. O. . |
| 8803932 | 6/1988 | World Int. Prop. O. . |

Primary Examiner—Patrick P. Garvin
Assistant Examiner—Brent M. Peebles
Attorney, Agent, or Firm—David M. Bunnell

[57] ABSTRACT

Hydrocarbon solvent solutions of alkylaluminoxane are made by mixing trimethylaluminum and a hydrocarbylaluminum compound, which compound contains at least one hydrocarbyl group having 2 or more carbon atoms, in a hydrocarbon solvent and thereafter adding water or a hydrated compound so as to form a solution of alkylaluminoxane in said solvent.

12 Claims, No Drawings

HYDROCARBON SOLUTIONS OF ALKYLALUMINOXANE COMPOUNDS

BACKGROUND

This invention relates generally to hydrocarbon solvent solutions of alkylaluminoxane compounds and more specifically to a process for preparing stable, hydrocarbon solvent solutions of alkylaluminoxanes by reacting a mixture of trimethylaluminum and an alkylaluminum compound with water or a hydrated compound.

Hydrocarbylaluminoxanes complexed with transition metal compounds have been found to be very effective olefin polymerization catalysts (Manyik et al. U.S. Pat. No. 3,242,099). Methylaluminoxane is an especially effective catalyst component. However, it has poor solubility in aliphatic hydrocarbon solvents which are preferred catalyst solvents because they are less toxic than aromatic hydrocarbons. Manufacturers of polymers which may come in contact with foodstuffs are concerned about solvent residues in their products and therefore seek to avoid the use of aromatic solvents during polymer production. Even in aromatic solvents, methylaluminoxane is not completely soluble such that the solutions become cloudy upon standing. Japanese application 63-87717 discloses the addition to aluminoxanes of branched chain alkylaluminum compounds in order to improve the solubility of aluminoxane compounds which can be formed from mixed alkoxyaluminum units which contain methyloxyaluminium compounds in proportions of about 30 to 70 mole percent. Long U.S. Pat. No. 3,639,378 discloses an aluminum trihydrocarbon compound modified with water where the hydrocarbon groups can be alike or different. Edwards, et al U.S. Pat. No. 4,772,736 discloses a process of preparing aluminoxanes by adding water to a solution of a hydrocarbylaluminum compound such as isobutyldihexylaluminum or diisobutylhexylaluminum. Sakhorovskaya et al, Zhurnal Obshchei Khimie, Vol. 32, No. 10, pp 3433-3438, October 1984 discloses the hydrolysis of sesquihexylisobutylaluminum to give monoisobutyltrihexyldialuminoxane. Chang U.S. Pat. No. 4,937,217 forms a mixed solution of trimethyl- and triethylaluminum in an aliphatic solvent with non-dehydrated silica gel to get a solid catalyst component of silica gel coated with aluminoxane. Kioka, et al. European published application 279,586 discloses forming finely divided aluminoxanes wherein one or more trialkylaluminums are directly reacted with water in a medium such as benzene, toluene, ethyl ether or tetrahydrofuran and then either adding an aluminoxane insoluble or sparingly soluble solvent, e.g., a linear or branched chain aliphatic hydrocarbon to the aluminoxane solution or spray drying. U.S. Pat. Nos. 4,189,402, 4,377,720 and 4,490,514 disclose aluminoxanes having mixed alkyl groups. Co-pending application Ser. No. 598,117, filed Oct. 16, 1990, provides improved hydrocarbon solvent solutions of alkylaluminoxane by adding a tri-n-alkylaluminum to preformed methylaluminoxane.

We have found a direct method for making clear, stable solutions of methylaluminoxane (MAO) compositions in hydrocarbon solvents and especially in aliphatic hydrocarbon solvents. The compositions have good activity as a polymerization catalyst component.

BRIEF SUMMARY

In accordance with this invention there is provided a process for making a hydrocarbon solvent solution of alkylaluminoxane comprising mixing trimethylaluminum and a hydrocarbylaluminum compound, which compound contains at least one hydrocarbyl group having 2 or more carbon atoms, in a hydrocarbon solvent and thereafter adding water or a hydrated compound so as to form a stable solution of alkylaluminoxane in said solvent.

Also provided in accordance with this invention are the hydrocarbon solvent solutions of alkylaluminoxane prepared by the above process.

DETAILED DESCRIPTION

Methylaluminoxane may exist in the form of a linear or cyclic polymer with the simplest compound being tetramethylaluminoxane, $(CH_3)_2AlOAl(CH_3)_2$. The compounds preferred for use in olefin polymerization usually contain about 9 to 20 of the repeating units.

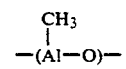

The compounds can be made, as is known in the art, by partial hydrolysis of trimethylaluminum (TMA) which is slurried or dissolved in an organic solvent such as toluene and treated with free water or a hydrated compound. The resulting methylaluminoxane product is usually a mixture of methylaluminoxane and trimethylaluminum. The alkylaluminoxanes prepared by the process of the invention have a mixture of methyl and higher alkyl groups which provide better solubility especially in aliphatic solvents.

The hydrocarbylaluminum compounds which are mixed with the trimethylaluminum can be represented by the formula $R_nAlH_{3-n}$ wherein n is an integer of 1 to 3 and when n=1, R represents a hydrocarbyl group containing at least 2 carbon atoms and when n=2 or 3, R represents hydrocarbyl groups, which can be the same or different at least one of which contains at least 2 carbon atoms. Preferably each alkyl group contains from 2 to about 20 carbon atoms more preferably has 5 to 12 carbon atoms. Di- or tri-alkylaluminum compounds having different alkyl groups can be used as well as monoalkylaluminum hydrides and mixtures of such alkylaluminum compounds. Trialkylaluminum compounds are preferred. Examples of suitable trialkylaluminum compounds include: triethylaluminum, tri-n-propylaluminum, tri-n-butylaluminum, triisobutylaluminum, tri-n-hexylaluminum, tri-n-octylaluminum, tri-n-decylaluminum, tri-n-dodecylaluminum, and the like. Higher alkylaluminum compounds such as tri-n-octylaluminum are most preferred because they provide modified methylaluminoxanes having excellent solubility with a minimum change in the catalytic properties compared to using conventional methylaluminoxanes prepared from trimethylaluminum alone.

Aliphatic hydrocarbons which can be used as solvents in the process and compositions of the invention include, for example, pentane, isopentane, hexane, cyclohexane, heptane, octane, decane, dodecane, hexadecane, octadecane and the like with those having carbon numbers of 5 to 10 being preferred. Aromatic hydrocarbons which can be used as solvents include benzene, toluene, xylene, cumene and the like with those having carbon numbers of 6 to 20 being preferred.

The proportions of trimethylaluminum to hydrocarbyl aluminum in the mixtures generally range from about 0.5 to 35 moles of trimethylaluminum per mole of hydrocarbylaluminum. Mole ratios of from about 1:1 to 10:1 are preferred, and mole ratios of from about 2:1 to 5:1 trimethylaluminum to hydrocarbylaluminum are most preferred. The amount of solvent used in forming the mixture is chosen to permit satisfactory temperature control during the hydrolysis reaction and to avoid the formation of aluminum oxide derivatives which precipitate and are difficult to filter. Generally an amount of solvent to provide concentrations of from about 5 to 15 weight percent total trimethylaluminum and hydrocarbylaluminum, based on the total weight of solution, are used.

The solvent mixture of trimethylaluminum and hydrocarbylaluminum can be hydrolyzed by adding either free water or water containing solids which can be either hydrates or are porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4 \cdot 5H_2O$, $Al_2(SO_4)_3 \cdot 18H_2O$, $FeSO_4 \cdot 7H_2O$, $AlCl_3 \cdot 6H_2O$, $Al(NO_3)_3 \cdot 9H_2O$, $MgSO_4 \cdot 7H_2O$, $ZnSO_4 \cdot 7H_2O$, $Na_2SO_4 \cdot 10H_2O$, $Na_3PO_4 \cdot 12H_2O$, $LiBr \cdot 2H_2O$, $LiCl \cdot 1H_2O$, $LiI \cdot 2H_2O$, $LiI \cdot 3H_2O$, $KF \cdot 2H_2O$, $NaBr \cdot 2H_2O$ and the like and alkali or alkaline earth metal hydroxides such as, for example, $NaOH \cdot 1H_2O$, $NaOH \cdot 2H_2O$, $Ba(OH)_2 \cdot 8H_2O$, $KOH \cdot 2H_2O$, $CsOH \cdot 1H_2O$, $LiOH \cdot 1H_2O$ and the like. Mixtures of any of the above hydrates can be used. The mole ratios of free water or water in the hydrate to total alkyl aluminum compounds in the mixture can vary widely, such as for example, from about 2:1 to 1:4 with ratio of from about 4:3 to 1:3.5 being preferred and about 1:1 most preferred.

Notwithstanding the above, the solvent mixture of trimethylaluminum and hydrocarbylaluminum has the advantage that water addition per se can be carried out with much better control of the reaction than by using trimethylaluminum alone.

The process can be carried out as known in the art in any apparatus which provides good and rapid mixing of the reactants such as, for example an agitator equipped vessel, a falling film reactor, a packed column or a tubular reactor. Suitable reaction temperatures can range from about $-30°$ to $60°$ C. and preferably $-10°$ to $20°$ C. The trimethylaluminum and hydrocarbylaluminum compound or compounds are premixed in the solvent for a sufficient time to permit alkyl group exchange to occur, although the exchange is normally instantaneous.

The invention is further illustrated by, but is not intended to be limited to, the following examples.

The alkylaluminoxane solutions of the invention retain the catalytic properties of unmodified methylaluminoxane and show high activity when used as olefin polymerization catalyst components.

The following examples were carried out under inert atmosphere conditions, using Schlenk glassware and vacuum line, in conjunction with an inert gas (nitrogen) dry box. Solvents were dried using standard methods. Filtration and vacuum distillation were done inside the inert gas (nitrogen) dry box and distillates were collected in a trap at $-78°$ C.

EXAMPLE 1

Trimethylaluminum (TMA) (11.2 g, 0.16 mol) and tri-n-octylaluminum (TNOA) (28.5 g, 0.08 mol) were dissolved in toluene (50 ml). The mixture was stirred at room temperature for 2 hours. $LiCl \cdot 1H_2O$ (14.2g, 0.24 mol) was suspended in toluene (350 ml) in a 3-neck flask equipped with a cooling jacket and a magnetic stirrer. The slurry was cooled to $-5°$ C. and the aluminumalkyl mixture was slowly added through a regulated dropping funnel during a period of about one hour. The mixture was then stirred at $10°$ C. overnight. The slurry was filtered and the solid residue washed with toluene. The resulting clear solution (430 g) contained 1.1 wt % Al, which is equivalent to 75% of the initial Al value.

EXAMPLE 2

TMA (11.2, 0.16 mol) and TNOA (28.5 g, 0.08 mol) were placed in toluene (200 ml) in a 3-neck flask equipped with a mechanical stirrer. The solution was cooled to $-20°$ C. While stirring, $LiBr \cdot 2H_2O$ (28.7 g. 0.24 mol) was slowly added in batches such that the reaction temperature was kept below $0°$ C. After addition, the reaction mixture was allowed to warm up slowly to room temperature. Total reaction time was about 6 hours. The slurry was filtered and washed with toluene. The product (219 g) contained 2.67 wt % Al, which is equivalent to 93% of the original Al value.

EXAMPLE 3

A mixture of TMA (11.2 g, 0.16 mol) and TNOA (28.5 g, 0.08 mol) was placed in a 3-neck flask, equipped with a magnetic stirrer and a regulated dropping funnel, containing toluene (200 ml). The mixture was first stirred at room temperature for 2 hours and then cooled to $-12°$ C. Water (4.3 g, 0.24 mol) was slowly added with extreme care. Despite the extreme care, the reaction due to the first few drops was rather violent (more dilution or smaller drops are required). Water was added such that the reaction temperature was below $-5°$ C. After addition, the reaction temperature was kept at $0°$ C. for about 2 hours and then allowed to warm up slowly to room temperature overnight. Total addition time was about 8 hours.

The mixture was difficult to filter even through a coarse frit, due to the very fine precipitate, presumably containing aluminum oxide derivatives. The product (215 g) was slightly cloudy and contained 2.15 wt % Al. The recovered aluminum value was 75%.

EXAMPLE 4

TMA (11.2 g, 0.16 mol) and TNOA (28.5 g, 0.08 mol) were placed in heptane (400 ml) in a 3-neck flask. The reaction was carried out as described in Example 3.

The final product (320 g 1.55 wt % Al) contained 77% of the initial aluminum value.

EXAMPLE 5

A heptane (700 ml) mixture of TMA (29.9 g, 0.41 mol) and TNOA (76.1 g, 0.21 mol) Was cooled to $-8°$ c. Water (11.2 g, 0.62 mol) was added slowly (syringe pump)while stirring with a magnetic stirrer. Addition was such that the reaction temperature was kept between $-5°$ C. and $-8°$ C. Total addition time was about 8 hours. The mixture was stirred at $-8°$ C. overnight and then kept at $0°$ C. for another 2 hours. The mixture was then filtered. The product (574 g, 2.25 wt% Al) contained 78% of the initial Al value.

EXAMPLE 6

TMA (11.2 g, 0.16 mol) and TNOA (28.5 g, 0.08 mol) were dissolved in Isopar C (400 ml) in a 3-neck flask equipped with a magnetic stirrer. The mixture was cooled to −20° C. Water (4.3 g, 0.24 mol) was slowly added via a syringe pump. Addition was such that the reaction temperature was kept between −14° C. and −16° C. After addition, the reaction temperature was kept at −6° C. overnight. The reaction mixture was allowed to warm up to +10° C. and then filtered. After work-up the clear product solution was found to contain 1.55 wt. % Al. Aluminum value recovered was 75%.

EXAMPLE 7

An Isopar C (400 ml) mixture of TMA (11.2 g, 0.16 mol) and TNOA (11.4 g, 0.031 mol) was hydrolyzed with water (3.4 g, 0.19 mol) as described in Example 6, except that the molar ratio TMA/TNOA was 5:1 instead of 2:1.

After work-up, 54% of the initial aluminum value was recovered.

EXAMPLE 8

A 5:1 molar mixture of TMA (15 g, 0.20 mol) and triisobutylaluminum (TIBA) (8.2g, 0.04 mol) in Isopar C (400 ml) was hydrolyzed with water (4.4 g, 0.24 mol) as described in Example 6, except that TIBA replaced TNOA. The product contained 55% of the initial aluminum value.

EXAMPLE 9

A main use of alkylaluminumoxanes is as a co-catalyst with a transitional metal compound in the polymerization of olefins to make polymers. Chemical analysis of various alkylaluminoxanes can be very similar even when the catalytic activity of the products differ greatly. For this reason the products are preferably evaluated using a polymerization test. One such test involves the polymerization of ethylene under pressure in dry toluene containing methylaluminoxane (MAO) and a zirconium compound. The amount of MAO, zirconium compound and ethylene is the same in each test. After the polymerization is complete, the polyethylene is recovered, dried and weighed. The test criteria is the amount of polyethylene formed.

Modified methylaluminoxanes (MMAO) prepared according to Examples 1-8 were used as co-catalysts in the polymerization of ethylene. Results showed that, within experimental error, these materials are almost as active as the unmodified MAO. A summary of the polymerization results is given in Table I.

TABLE I

| Example | Mole Ratio TMA/TNOA | Hydrolyzing[a] Agents | Solvent | Relative Activity[b,c] |
|---|---|---|---|---|
| 1 | 2/1 | LiCl•H$_2$O | Toluene | 92 |
| 2 | 2/1 | LiBr•2H$_2$O | Toluene | 75 |
| 3 | 2/1 | H$_2$O | Toluene | |
| 4 | 2/1 | H$_2$O | Heptane | 80 |
| 5 | 2/1 | H$_2$O | Heptane | 77 |
| 6 | 2/1 | H$_2$O | Isopar C | 79 |
| 7 | 5/1 | H$_2$O | Isopar C | 96 |
| 8 | 5/1 (TIBA) | H$_2$O | Isopar C | 93 | a. One mole H$_2$O/mole aluminum
b. Unmodified MAO - 96, based on yield of polyethylene obtained.
c. Bis(cyclopentadienyl)zirconium dichloride as the other catalyst.

The process of the invention as illustrated above directly provides clear stable solutions of modified methylaluminoxanes in hydrocarbon solvents, and especially aliphatic hydrocarbon solvents in which normal MAO's are not stable. The methylaluminoxanes have good polymerization activity.

What is claimed is:

1. A process for making a hydrocarbon solvent solution of alkylaluminoxane comprising mixing trimethylaluminum and a trialkylaluminum compound wherein each alkyl group contains 4 to 20 carbon atoms, in a hydrocarbon solvent and thereafter adding water or a hydrated compound so as to form a solution of alkylaluminoxane in said solvent.

2. The process according to claim 1 wherein from about 0.5 to 35 mole of trimethylaluminum per mole of trialkylaluminum compound is from about 2:1 to 1:4.

3. The process according to claim 2 wherein the trialkylaluminum compound is selected from tri-n-hexylaluminum, tri-n-octylaluminum and triisobutylaluminum.

4. The process according to claim 3 wherein the trialkylaluminum compound is tri-n-octylaluminum, from about 2 to 5 mole of trimethylaluminum per mole of tri-n-octylaluminum are mixed in an aliphatic solvent and the mole ratio of water or water in the hydrate to the total moles of trimethylaluminium and tri-n-octyl aluminum is from about 4:3 to 1:3.5.

5. The process according to claim 4 wherein the hydrate is selected from LiOH.1H$_2$O and LiBr.2H$_2$O.

6. A hydrocarbyl solvent solution of alkylaluminoxane prepared by the process comprising mixing trimethylaluminum and a trialkylaluminum compound wherein each alkyl group contains 4 to 20 carbon atoms, in a hydrocarbon solvent and thereafter adding water or a hydrated compound so as to form a solution of alkylaluminoxane in said solvent.

7. The hydrocarbon solvent solution of claim 6 wherein from about 0.5 to 35 mole of trimethylaluminum per mole of trialkylaluminum compound are mixed and the mole ratio of water, or water in the hydrate, to the total moles of trimethylaluminum and hydrocarbyl aluminum compound is from about 2:1 to 1:4.

8. The hydrocarbon solvent solution of claim 7 wherein the trialkylaluminum compound is selected from tri-n-hexylaluminum, tri-n-octylaluminum and triisobutylaluminum.

9. The hydrocarbon solvent solution of claim 8 wherein the trialkylaluminum compound is tri-n-octylaluminum, from about 2 to 5 mole of trimethylaluminum per mole of tri-n-octylaluminum are mixed in an aliphatic solvent and the mole ratio of water or water in the hydrate to the total moles of trimethylaluminium and tri-n-octyl aluminum is from about 4:3 to 1:3.5.

10. The hydrocarbon solvent solution of claim 9 wherein the hydrate is selected from LiOH•1H$_2$O and LiBr•2H$_2$O.

11. The process of claim 4 wherein about 5 moles of trimethylaluminum per mole of tri-n-octylaluminum are mixed.

12. The hydrocarbon solvent solution of claim 6 wherein about 5 moles of trimethylaluminum per mole of tri-n-octylaluminum are mixed.

* * * * *

UNITED STATES PATENT AND TRADEMARK OFFICE
CERTIFICATE OF CORRECTION

PATENT NO. : 5,157,008
DATED : Oct. 20, 1992
INVENTOR(S) : SAMUEL A. SANGOKOYA, ET AL.

It is certified that error appears in the above-identified patent and that said Letters Patent is hereby corrected as shown below:

In the Claims:

Col. 6, line 24, Claim 2, reads:

"trialkylaluminum compound is from about 2:1 to 1:4."

but should read:

-- trialkylaluminum compound are mixed and the mole ratio of water, or water in the hydrate, to the total moles of trimethylaluminum and trialkylaluminum compound is from about 2:1 to 1:4. --

Signed and Sealed this

Twelfth Day of October, 1993

Attest:

BRUCE LEHMAN

Attesting Officer

Commissioner of Patents and Trademarks